US006454798B1

United States Patent
Moe

(10) Patent No.: US 6,454,798 B1
(45) Date of Patent: Sep. 24, 2002

(54) POLYMER HEART VALVE WITH HELICAL COAPTION SURFACE

(75) Inventor: Riyad Moe, Austin, TX (US)

(73) Assignee: Sulzer Carbomedics Inc., Austin, TX (US)

(*) Notice: Subject to any disclaimer, the term of this patent is extended or adjusted under 35 U.S.C. 154(b) by 0 days.

(21) Appl. No.: 09/746,379

(22) Filed: Dec. 21, 2000

(51) Int. Cl.[7] .................................................. A61F 2/06
(52) U.S. Cl. ..................................... 623/2.12; 623/2.15
(58) Field of Search ............................... 623/2.12, 2.13, 623/2.15, 2.1, 2.33, 901, 909

(56) References Cited

U.S. PATENT DOCUMENTS 4,888,009 A * 12/1989 Lederman et al. ......... 623/2.19

FOREIGN PATENT DOCUMENTS

GB         WO 98/32400    * 7/1998 ............. A61F/2/24
WO         WO 00/53125    * 9/2000 ............. A61F/2/24

* cited by examiner

*Primary Examiner*—David J. Isabella
*Assistant Examiner*—Urmi Chattopadhyay
(74) *Attorney, Agent, or Firm*—Timothy L. Scott

(57) ABSTRACT

A polymer heart valve has a leaflet with a base geometry of a cylinder for simplicity and effective opening. A helical swept surface is added to the top of the cylinder to enhance stable coaption. The heart valve includes a plurality of flexible leaflets. Each leaflet includes a top portion and a bottom portion. The bottom portion is an axial section of a cylinder having an axis and a radius. A first section of the top portion is a surface defined by a first arc having a first radius swept along a first helix. The first arc is tangent to the axial section of the cylinder. A second section of the top portion is a surface defined by a second arc having a second radius swept along a second helix. The second arc is tangent to the axial section of the cylinder. The second helix is a left-handed helix having the same radius and axis as the cylinder.

20 Claims, 5 Drawing Sheets

POLYMER HEART VALVE WITH HELICAL COAPTION SURFACE

TECHNICAL FIELD

The disclosures herein relate generally to prosthetic heart valves and more particularly to tri-leaflet prosthetic heart valves having polymeric valve leaflets.

BACKGROUND

Prosthetic heart valves for human patients have been available since the 1950s, following the advent of blood oxygenators, which made open heart surgery possible. Today, there are three general types of prosthetic heart valves, including mechanical valves, tissue valves and polymer valves. A heart valve prosthesis is implanted into an annular opening in a patient's heart following surgical removal of a diseased or damaged natural valve. The valve can be secured in the annulus of the opening through the use of sutures or pins that penetrate the host tissue and an outside edge of the valve. Alternatively, the valve can be secured in the annulus by suturing the host tissue to a sewing ring. Heart valves function essentially as one-way check valves for blood flow through the beating heart.

The term "mechanical valve" as used herein refers to bi-leaflet heart valves comprising a valve orifice fabricated at least in part of a rigid, biologically compatible material such as pyrolytic carbon, and comprising essentially no biological components. The term "bioprosthetic valve" refers to a bi-leaflet or tri-leaflet heart valve comprising at least some biological components such as tissue or tissue components. The biological components of tissue valves are obtained from a donor animal (typically bovine or porcine), and the valve may comprise either biological materials alone or biological materials with man-made supports or stents. The term "polymeric valve" refers to a tri-leaflet or bi-leaflet heart valve comprising at least some elastomeric polymer components, including at least elastomeric polymer valve leaflets.

A bi-leaflet mechanical valve typically comprises an annular valve body in which two opposed leaflet occluders are pivotally mounted. The occluders are typically rigid, although some designs incorporate semi-rigid leaflets, and the occluders move between a closed position, in which the two leaflets are mated and block blood flow in the reverse direction, and an open position, in which the occluders are pivoted away from each other and do not block blood flow in the forward direction. The energy of blood flow causes the occluders to move between their open and closed positions.

Flexible heart valves seal against reverse flow by having leaflets whose total surface area is greater than the area of the orifice. Sections of the leaflets, therefore, contact one another, or coapt, to close the valve and prevent blood backflow. Coaptive sealing occurs over an area on the leaflets, rather than merely along their edges. Two leaflets are unlikely to seal with any stability if they only contact line to line. This can cause T-boning, or prolapse. T-boning occurs when the end of one leaflet slips below the end of the mating leaflet during closing, forming a line-on-line contact rather than an area contact.

Although both tissue and polymer valves involve flexible leaflets, the degree of control possible for the shape of tissue valve leaflets is extremely small, since the leaflets are formed from tissue sheets that are trimmed and sewn to a valve stent. Polymer valves, on the other hand, may be fabricated by molding, casting, and other known techniques, and therefore allow much greater control of valve body and leaflet shape. By precise control of the leaflet shape, polymer heart valves may be fabricated with improved wear and performance characteristics. In particular, by providing leaflets having an analytic shape in a selected position which can be represented generally by analytic geometry. An analytic shape may include a portion of a cylindrical surface, of an ellipsoid, of a paraboloid, or of another shape that can be defined mathematically.

A tri-leaflet heart valve prosthesis typically comprises an annular valve body and three flexible leaflets attached thereto. The valve body comprises an annular base and three leaflet support posts. A sewing ring annularly coupled to the periphery of the valve body provides a place for sutures to be applied when the valve is implanted. The leaflets are attached to the three shaped posts along an attachment curve, and they also each have a free, unattached edge remote from the attachment curve. The place where two adjacent leaflets come together at one of the support posts is called the commissure, and the generally curved area on the leaflet between the free edge and the attachment curve is known as the belly of the leaflet. The free edges of the three leaflets come together at a "triple point" generally on the axis of the valve.

One aspect of the sealing problem for tri-leaflet polymer valves arises from the nature of the valve geometry. As already noted, it is desirable to provide leaflets defined by an analytical shape. Tradeoffs must be made, however, among various possible geometries. In particular, it is desirable to provide a coaption surface that seals efficiently and robustly. Many prior art approaches to the difficult problem of leaflet design have been made.

U.S. Pat. No. 4,888,009 shows a prosthetic heart valve comprising leaflets of a spherical section, with no additional coaption surface. While this design is simple to fabricate, provides relatively good fabrication control, and has a small gap between leaflets, the vertical component of the angle between the surface tangents of opposed leaflets is not constant. For example, at the triple point and commissures, the leaflet surface tangent is nearly vertical, so the angle between the surface tangents of opposed leaflets is small and an effective and robust seal is facilitated in these regions. However, at the midpoint of the leaflet free edge between the commissures and the triple point, the leaflet surface tangent is much further from vertical. Consequently, the angle between the surface tangents of opposed leaflets is large, and the seal may not be effective or robust. Small deviations in position or load might disrupt the sealing of the leaflets and cause one free margin to slide below the other. The leaflets would have a line of contact instead of an area of contact.

Coaptive surfaces at the ends of the leaflet can be used to prescribe the angle between the surface tangents at the ends of opposing leaflets. The simplest shape for a coaptive surface is to have a vertical surface (i.e., a surface oriented generally parallel to the direction of blood flow) at the end of each leaflet. Such surfaces appear to be vertically aligned when the valve is in the closed position. For a tri-leaflet valve with identical leaflets, two vertical coaption surfaces are actually needed on each leaflet because each leaflet covers 120 degrees (not 180), and the leaflets must bend inward from the commissure to the triple point before again bending back to the other commissure (see FIG. 3). Tri-leaflet valves having vertical coaption surfaces, therefore, all have three general surface areas: the belly of the leaflet and the two coaptive surfaces. Many leaflet belly surface configurations have been proposed (with and without vertical coaption surfaces). Tri-leaflet valves having vertical coaption surfaces all suffer from a particular problem. Although the sealing of two vertical surfaces is effective, the discontinuous crease which transitions the coaptive surface to the leaflet belly resists the reverse buckling needed to open the valve. The result is high opening pressures and high pressure drops across the open valve.

In addition to leaflets comprising a single analytical shape, attempts have been made to improve valve performance by fabricating leaflets comprising more than one analytical shape. In this regard, WO 98/32400 provides a valve having leaflets comprising a cylindrical section and having a spherical coaption end. The transition from the leaflet belly to the coaption surface is made by revolving an arc around an axis to form a spherical coaption area. In addition, the specific shape chosen allows the surface tangencies at the leaflet free edges to be vertical. The designers conclude that bidirectional curvature in the leaflet belly produces poor opening characteristics, and that leaflets with only one degree of curvature in the belly are superior. Although the WO 98/32400 valve provides better performance than a fully spherical leaflet or a fully cylindrical leaflet, the valve has relatively large gaps at the triple point and the commissure.

General engineering experience with tissue and polymer heart valves have established a number of criteria for these valves, including:

1) A coaption surface which extends from the triple point to the commissure.
2) A coaption surface which is tangent to the belly geometry at its bottom and nearly vertical at its top.
3) A simple, singly curved leaflet belly.
4) A height short enough to fit into the natural anatomy.
5) A small gap area between leaflets to reduce regurgitation.

Cylindrical leaflets with revolved leaflet end sections e.g. spheres and toroids, produce adequate topological solutions for only a limited range of valve heights and gap areas. Given the limitations of existing leaflet geometries, it is desirable to have a valve leaflet defined by an analytic shape that provides a smooth transition surface from the leaflet belly to the coaption area, but which avoid large gaps at the commissures and the triple point. Analytical shapes suggested in the prior art have not achieved these goals. Therefore, what is needed is a new valve surface topology with more degrees of freedom so that a shorter valve with a small gap area, a cylindrical leaflet, and a tangent coaptive surface can be produced.

SUMMARY OF THE INVENTION

It has been discovered that a heart valve with leaflets having a helical swept coaption surface provides advantages not obtained from prior art analytical leaflet shapes. In one embodiment, accordingly, the present invention provides a valve leaflet having a base portion geometry comprising a cylindrical section and a top portion geometry comprising a swept helix. To this end, a heart valve includes a plurality of flexible leaflets. Each leaflet includes a top portion and a bottom portion. The bottom portion is a cylinder having an axis, a radius and an axial section. A first section of the top portion is a surface defined by a first arc swept along a first helix. The first helix is a right handed helix having the same radius and axis as the cylinder. A second section of the top portion is a surface defined by a second arc swept along a second helix. The second helix is a left handed helix having the same radius and axis as the cylinder.

BRIEF DESCRIPTION OF THE DRAWING FIGURES

DETAILED DESCRIPTION OF PREFERRED EMBODIMENTS

Figure 1:
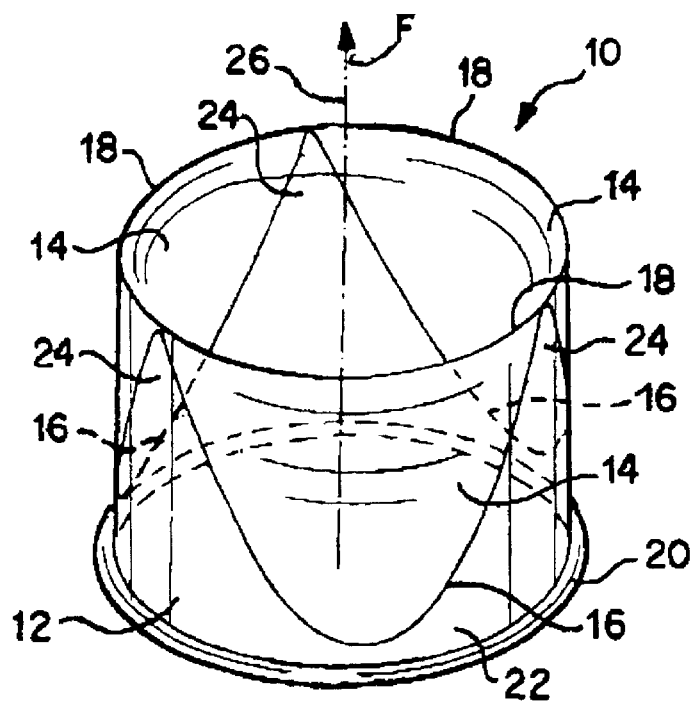
FIG. 1 is a perspective view illustrating an embodiment of a polymer valve in an open position.

A tri-leaflet heart valve prosthesis 10 comprises an annular, generally cylindrical elastomeric valve body 12 and three flexible leaflets 14 made of a biocompatible polymer such as silicone or polyurethane, as shown in FIG. 1. Each leaflet has an attachment edge by which it is coupled to the valve body along an attachment curve 16. Each leaflet has a free edge 18 that is not coupled to the valve body. A sewing ring 20 may be coupled to the base of the valve body 12 to provide a place for sutures to be applied when the valve is implanted. The valve body 12 comprises an annular base 22 and a leaflet support, comprising three shaped posts 24, that support the leaflets 14.

Figure 2:
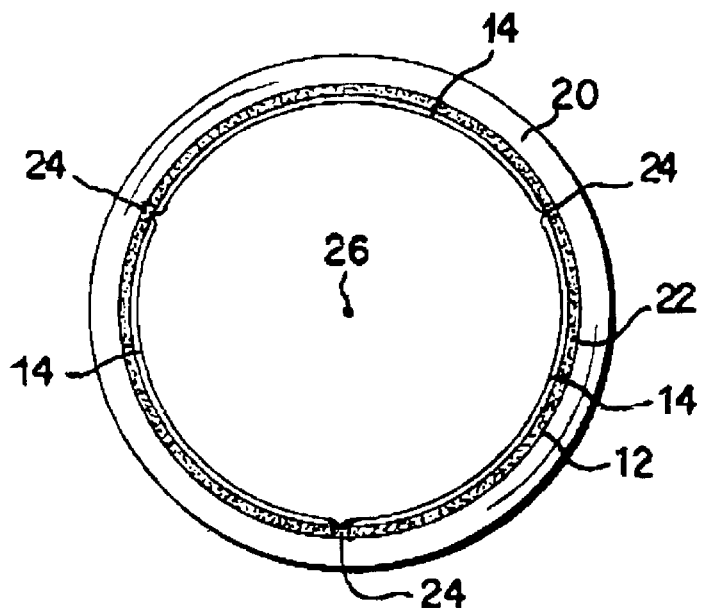
FIG. 2 is a top view of the polymer valve of FIG. 1.

When fluid flow is in the forward direction, i.e. in the direction of the arrow F shown in FIG. 1, the pressure of the blood flow causes the leaflets 14 to deflect away from a central longitudinal axis 26 of the valve body that is generally parallel to the three posts 24. In this "open" position, the leaflets 14 define a large flow orifice, as shown in FIGS. 1 and 2. With the leaflets in the open position, the valve presents little resistance to fluid flow.

Figure 3:
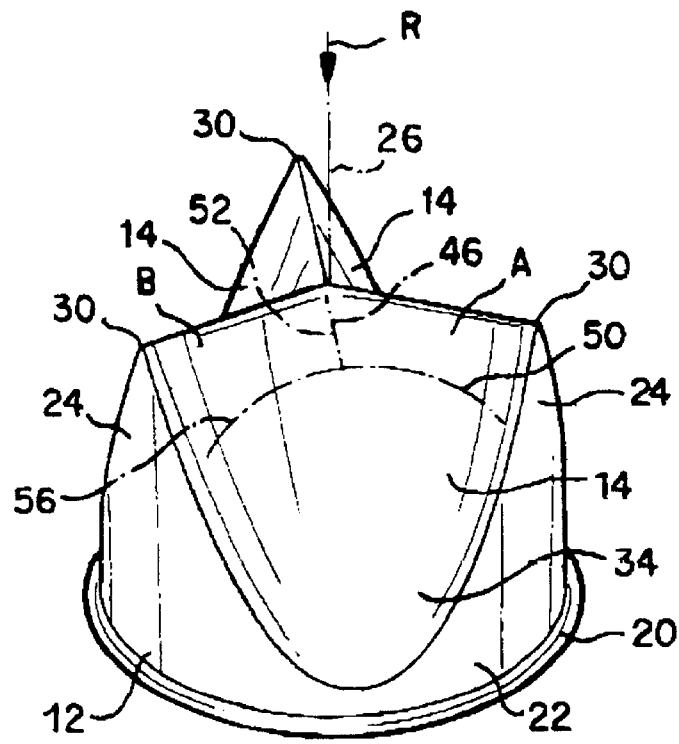
FIG. 3 is a perspective view illustrating an embodiment of a polymer valve in a closed position.
Figure 4:
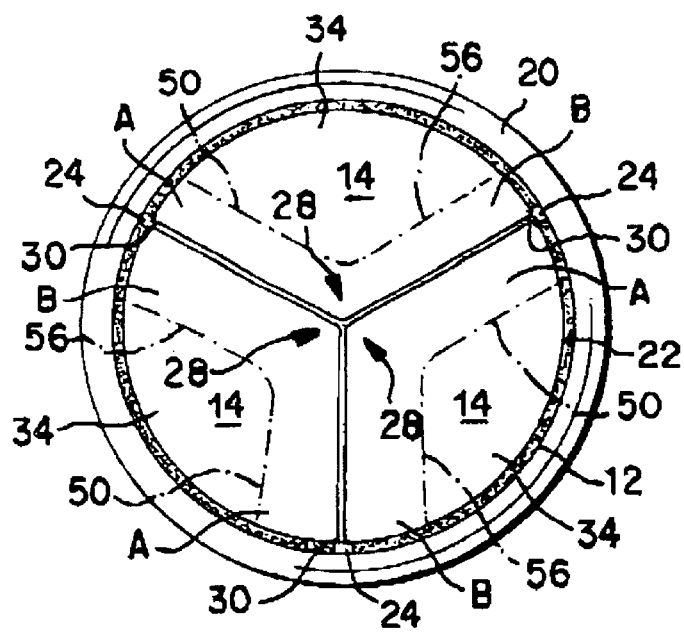
FIG. 4 is a top view of the polymer valve of FIG. 3.

When fluid flow is in the reverse direction, i.e. in the direction of the arrow R shown in FIG. 3, the pressure of the blood flow causes the leaflets 14 to deflect toward axis 26, as shown in FIGS. 3 and 4. In this "closed" position, each leaflet would occlude more than one-third of the valve body's orifice were it not for the presence of the other leaflets. Consequently, when the three leaflets deflect toward axis 26, they engage each other and form coaptive areas along the free edges 18, which help the valve seal against reverse flow. Further, when the leaflets press together, each leaflet forms a "triple point" 28 at the point where the three leaflets come together, as shown in FIG. 4. The place where the leaflets 14 come together adjacent the posts 24 is called the "commissure" 30, as shown in FIG. 3.

Figure 5:
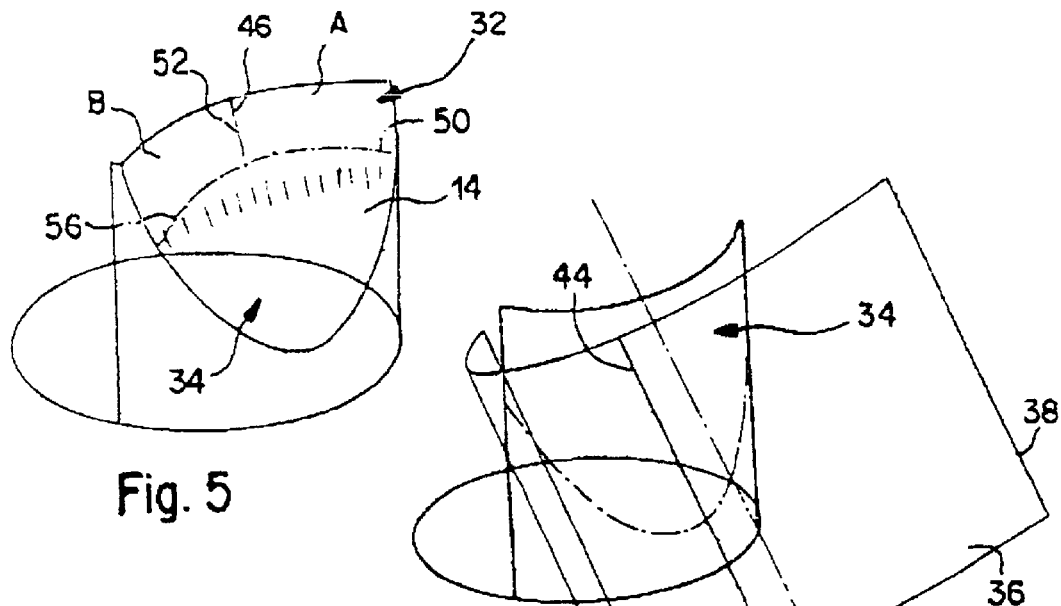
FIG. 5 is a perspective view illustrating an embodiment of a partial valve body and a single leaflet.
Figure 6:
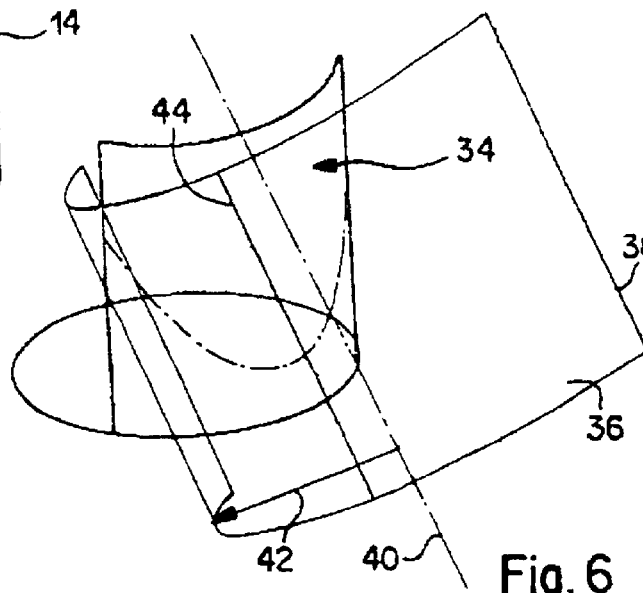
FIGS. 6–11 are perspective views illustrating a method of forming the leaflet of FIG. 5.
Figure 7:
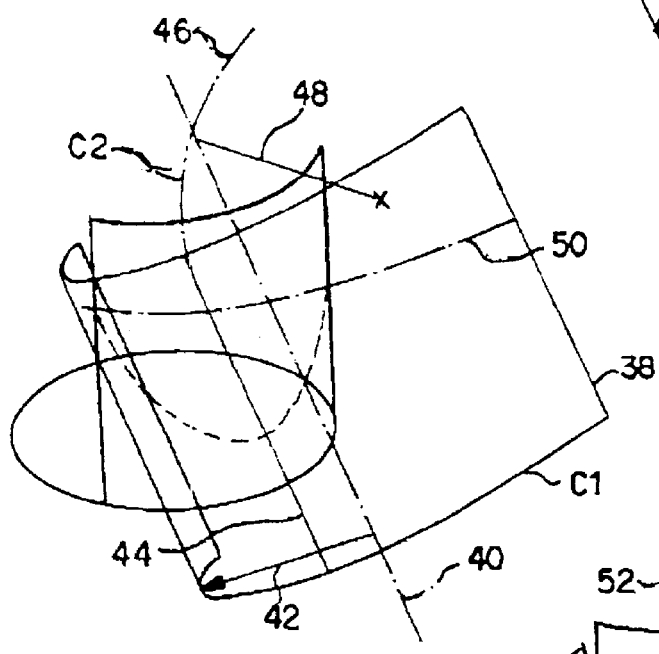
Figure 8:
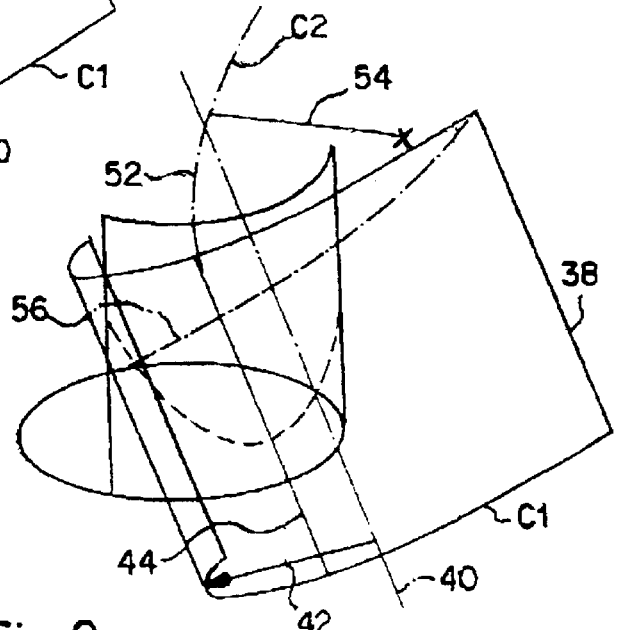
Figure 10:
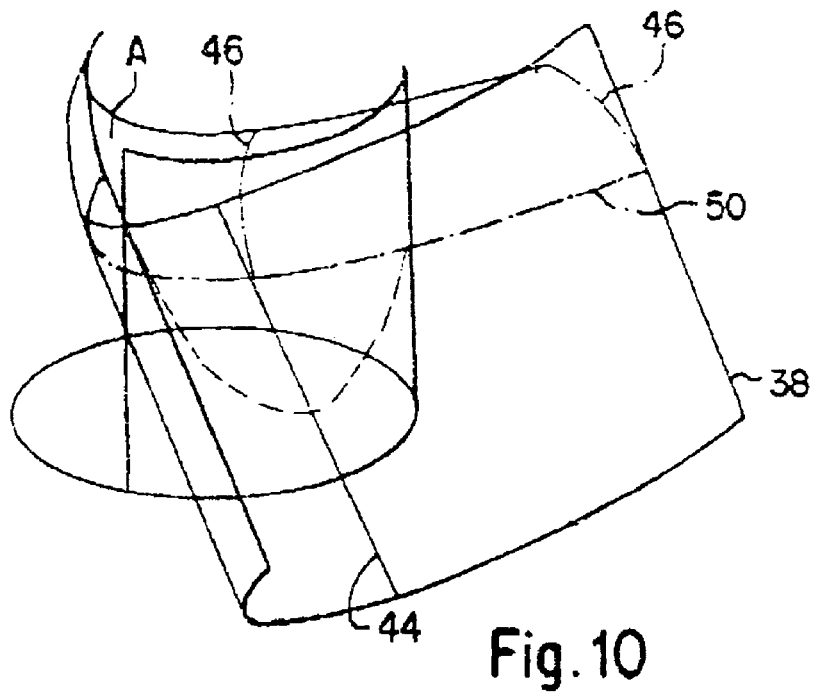
Figure 11:
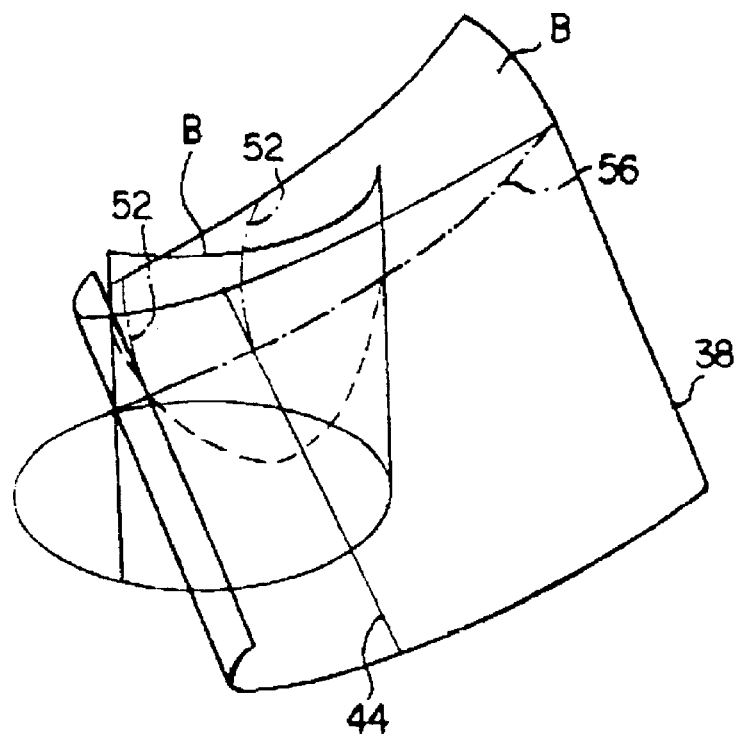

Each leaflet 14 of heart valve 10 includes a top portion 32 and a bottom portion 34, FIG. 5. The bottom portion 34 is formed of a surface 36, see also FIG. 6, defined as a cylinder 38 having an axis 40, a radius 42 and an axial section 44. A first section A, FIG. 5, of the top portion 32 is a surface defined by a first arc 46, FIGS. 7 and 10, having a first radius 48, said first arc 46 being swept along a first helix 50. The first arc 46 is preferably tangent to the axial section 44 of the cylinder 38, as shown in FIG. 7. The first helix 50 is a right-handed helix having the same radius 42 and axis 40 as the cylinder 38. A second portion B, FIG. 5, of the top portion 32 of leaflet 14 is a surface defined by a second arc 52, FIGS. 8 and 11, having a second radius 54, said second arc being swept along a second helix 56. The second arc 52 is preferably tangent to the axial section 44 of the cylinder 38, as shown in FIG. 11. The second helix 56 is a left-handed helix having the same radius 42 and axis 40 as the cylinder 38. The first portion A and the second portion B provide two coaption surfaces, each surface extending from the triple point to a commissure. Each coaption surface is tangent to the belly geometry of the bottom portion 34 at the bottom of the coaption surface and nearly vertical at the top of the coaption surface.

Figure 9:
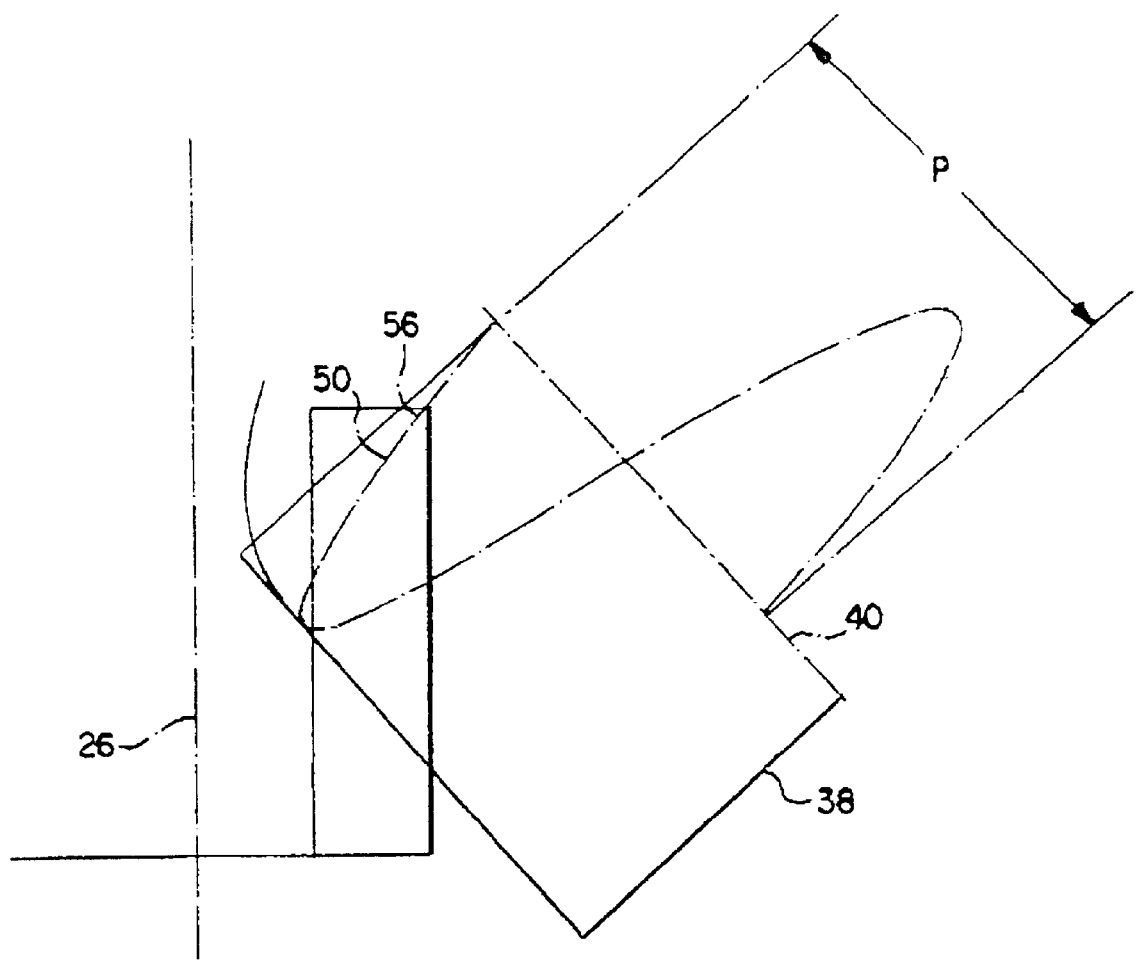

The first helix 50 has a pitch P, FIG. 9, and the second helix 56 has an equal pitch P. Also, the first radius 48 is equal to the second radius 54. As a result of this construction, the surface 36 of bottom portion 34 has a curvature C1 defined by radius 42. However, each of the first section A and the second section B of the top portion 32 also have the curvature C1 and a curvature C2 defined by radii 48 and 54, respectively, to improve coaption at the free edges 18.

Embodiments of the present invention provide leaflets having a smooth surface transition between the bottom portion and top portion thereof. In addition, the edges of the leaflets are substantially closer to each other when the valve is in the unloaded ("at rest") position, resulting in a smaller gap between the leaflets. The valve has improved closure characteristics.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A heart valve comprising:
   a body;
   a plurality of flexible leaflets attached to the body, each leaflet including a top portion and a bottom portion;
   the bottom portion being a surface defined as a cylinder having an axis, a radius and an axial section;
   a first section of the top portion being a surface defined by a first arc having a first radius, said first arc being swept along a first helix, the first helix being a right handed helix having the same radius and axis as the cylinder; and
   a second section of the top portion being a surface defined by a second arc having a second radius, said second arc being swept along a second helix, the second helix being a left handed helix having the same radius and axis as the cylinder.

2. The valve as defined in claim 1 wherein the first helix has a first pitch and the second helix has a second pitch equal to the first pitch.

3. The valve as defined in claim 1 wherein the first radius is equal to the second radius.

4. The valve as defined in claim 1 wherein the surface of the bottom portion has a curvature in one direction and the surface of each of the first and second top portions has a curvature in multiple directions.

5. The valve as defined in claim 1 including three identical leaflets.

6. A heart valve comprising:
   a body;
   a plurality of flexible leaflets attached to the body, each leaflet including a top portion and a bottom portion;
   the bottom portion being a surface defined as a cylinder having an axis, a radius and a naxial section;
   a first section of the top portion being a surface defined by a first arc swept along a first helix, the first arc being tangent to the axial section of the cylinder, the first helix being a right handed helix having the same radius and axis as the cylinder; and
   a second section of the top portion being a surface defined by a second arc swept along a second helix, the second arc being tangent to the axial section of the cylinder, the second helix being a left handed helix having the same radius and axis as the cylinder.

7. The valve as defined in claim 6 wherein the first helix has a first pitch and the second helix has a second pitch equal to the first pitch.

8. The valve as defined in claim 6 wherein the first arc has a first radius and the second arc has a second radius and the first radius is equal to the second radius.

9. The valve as defined in claim 6 wherein the surface of the bottom portion has a curvature in one direction and the surface of each of the first and second top portions has a curvature in multiple directions.

10. The valve as defined in claim 6 including three identical leaflets.

11. The valve as defined in claim 6 wherein the leaflets are formed of a synthetic material.

12. A method of forming a heart valve comprising:
   providing a body;
   attaching a plurality of leaflets to the body;
   providing a top portion and a bottom portion for each leaflet;
   forming the bottom portion from a cylinder having an axis, a radius and an axial section;
   forming a first section of the top portion by sweeping a first arc along a first helix, wherein the first helix is a right handed helix having the same radius and axis as the cylinder; and
   forming a second section of the top surface by sweeping a second arc along a second an axial section;
   a first section of the top portion being a surface defined by a first arc having a first radius, said first arc being swept along a first helix, the first helix being a right handed helix having the same radius and axis as the cylinder; and
   a second section of the top portion being a surface defined by a second arc having a second radius, said second arc being swept along a second helix, the second helix being a left handed helix having the same radius and axis as the cylinder.

13. The method as defined in claim 12 wherein the first helix has a first pitch and the second helix has a second pitch equal to the first pitch.

14. The method as defined in claim 12 wherein said first arc has a first radius and said second arc has a second radius and the first radius is equal to the second radius.

15. The method as defined in claim 12 wherein the plurality of leaflets includes three leaflets.

16. A method of forming a heart valve comprising:
   providing a body;
   attaching a plurality of leaflets to the body;
   providing a top portion and a bottom portion for each leaflet;
   forming the bottom portion from a cylinder having an axis, a radius and an axial section;
   forming a first section of the top portion by sweeping a first arc having a first radius along a first helix, the first arc being tangent to the axial section of the cylinder, wherein the first helix is a right handed helix having the same radius and axis as the cylinder; and forming a second section of the top surface by sweeping an arc having a second radius along the second helix, the second arc being tangent to the axial section of the cylinder, the second helix being a left handed helix having the same radius and axis as the cylinder.

17. The method as defined in claim 16 wherein the first helix has a first pitch and the second helix has a second pitch equal to the first pitch.

18. The method as defined in claim 16 wherein the first radius is equal to the second radius.

19. The method as defined in claim 16 wherein the plurality of leaflets includes three leaflets.

20. The method as defined in claim 16 wherein the leaflets are formed of a synthetic material.

\* \* \* \* \*